Sept. 13, 1938.

B. MOLLER

Re. 20,858

HAND GUARD

Original Filed June 5, 1933

INVENTOR.
BERNIECE MOLLER
BY
Harry C. Schroeder
ATTORNEY

Reissued Sept. 13, 1938 Re. 20,858

UNITED STATES PATENT OFFICE 20,858

HAND GUARD

Berniece Moller, Piedmont, Calif.

Original No. 1,984,613, dated December 18, 1934, Serial No. 674,270, June 5, 1933. Application for reissue October 20, 1936, Serial No. 106,585

14 Claims. (Cl. 128—133)

The invention is for an improved hand guard, and more particularly for a guard in the nature of a cuff to be secured to an infant's wrist which will surround the hand and thereby prevent the infant from putting its thumb or any of its fingers into its mouth.

The primary object of the invention is to construct a device of the character indicated which will prevent an infant from putting its thumb or any of its fingers into its mouth, while at the same time not interfere with a free and untrammeled normal movement of the hand and fingers of the infant within the guard, yet permit the hand to grasp things extended into the open outer end of the cuff, such as a rattle or toy.

A further object being to so construct a guard that it will eliminate any danger of discomfort or injury to the infant's hand such as chafing or cutting by rough or sharp edges coming in contact therewith.

A still further object of the invention is to so construct such a device that it will be absolutely effective, comfortable, simple and economical of manufacture, and readily adjusted to the hands of an infant.

The invention will be hereinafter fully set forth and particularly pointed out in the claims.

In the accompanying drawing.

Like reference characters indicate like parts throughout the several figures of the drawing.

Figure 1:
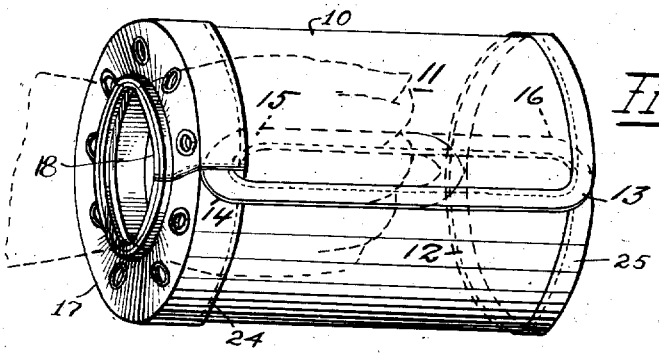
Figure 1 is a side elevation showing the guard attached to the wrist of an infant, the wrist and hand being shown in dotted lines.
Figure 2:
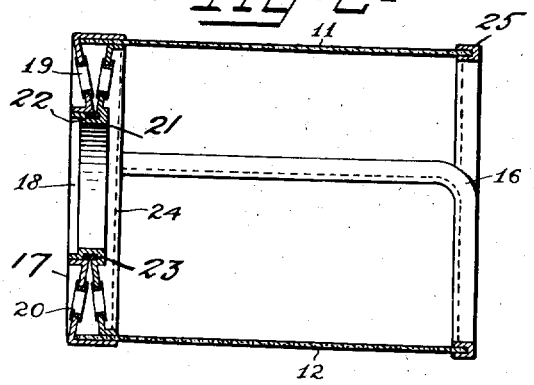
Figure 2 is a central vertical section.
Figure 4:
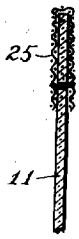
Figure 4 is a vertical sectional view of the bottom portion of the side wall of one of the guard members showing the protective binding stitched thereto.
Figure 3:
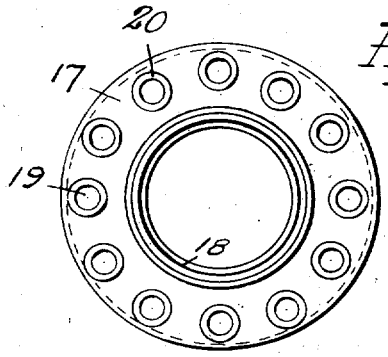
Figure 3 is a top plan view showing ventilating apertures therethrough.
Figure 5:
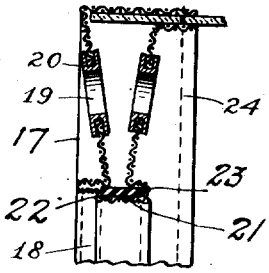
Figure 5 is an enlarged view of the cuff portion.

Reference character 10 indicates the guard as a whole which as here shown comprises two preferably transparent transversely arcuate members made of transparent material such as celluloid. 11 and 12 indicate the respective arcuate members forming the guard which are slightly more than 180° of a circle and are nosed or rounded at their respective upper and lower corners as at 13, 14, 15 and 16, the side edges of one of the members overlapping the side edges of the other of the members, as clearly shown in Figure 1.

From the foregoing it will be readily appreciated that any outward pressure exerted on the members 11 and 12 by movement of the infant's hand within the guard will cause the members 11 and 12 to swing outwardly from the bottom, the soft cover 17 functioning as a hinge which permits limited pivotal movement of the sections thereby affording free and normal use of the hand within the guard, while at the same time effectively preventing the insertion by the infant of any part of its hand in its mouth.

Cover 17, which is preferably made of a soft material such as yarn, is provided with a central opening 18 for the insertion therethrough of an infant's hand and wrist. The cover 17 is provided with ventilating apertures 19 which may be surrounded by metallic eyelets 20 to prevent the closing of the apertures and thereby assuring an absolutely free circulation of air through the guard to avoid perspiration of the infant's hand. The cover 17 is preferably made of a single piece of material, though not necessarily so and is folded back upon itself as at 21, forming a channel 22 in which is secured an elastic band 23 for holding the guard snugly about infant's wrist as is clearly shown in Figure 1. It should also be noted that as the band 23 contracts about the baby's wrist, a pull exerted upon the cover or head 17 radially thereof will tend to hold the sections in the overlapped relation shown in Figure 1 and yieldably resist movement of the sections away from each other. The outer or free edges of cover 17 are secured to the top of the side walls of the guard members 11 and 12 by stitching 24 or in any preferred manner.

The lower edges of guard members 11 and 12 are provided with a soft binding material 25 which may be stitched or otherwise secured thereto to prevent chafing or cutting the infant's hands by the edges of these members.

While Figure 1 indicates the guard cuff as a shell made of two pieces, it is manifest that it may be of but one piece if desired.

What is claimed is:

1. A hand guard comprising a cylindrical body composed of a plurality of transversely arcuate sections having overlapping side edges and a yieldable cover for one end of said body formed with a hand opening and being attached to ends of said sections and mounting the sections for limited tilting movement relative to each other.

2. A hand guard comprising a cylindrical body composed of a plurality of transversely arcuate sections having their side edge portions disposed in overlapping relation to each other, and a yieldable cover for one end of said body provided with a hand opening and having marginal portions secured about ends of said sections, said cover mounting said sections for limited pivotal movement relative to each other.

3. A hand guard comprising a cylindrical body composed of a plurality of transversely arcuate sections having overlapping side edges, and a yieldable cover for one end of said body formed with a hand opening and being attached to ends of said sections and mounting the sections for limited pivotal movement relative to each other, said cover being provided with ventilating openings, and eyelets secured in said openings to reinforce material bordering the openings.

4. A hand guard comprising a cylindrical body open at its front end and formed of transversely arcuate sections having overlapped side edge portions, a yieldable cover for the rear end of said body secured to ends of said sections, said cover being formed with a hand opening, and an elastic band secured to the cover around the opening to hold the cover snugly in place about a baby's wrist, the yieldable cover permitting limited pivotal movement of said sections relative to each other from their rear ends.

5. A hand guard comprising a cylindrical body open at one end and formed of sections having overlapped side edge portions, a yieldable cover at the other end of said body formed of fabric and stitched about its margins to ends of said section, said cover being provided with an opening, a channel being formed in the cover around the opening, and an elastic member within the channel to draw the cover about a baby's wrist and yieldably resist spreading of the sections.

6. An anti-thumb-sucking device for infants comprising a cuff of transparent semi-rigid material of a size to enclose a baby's hand and extend outwardly beyond the same, said cuff provided with means at one end of the cuff for securing around the wrist, the outer end of the cuff being open and unobstructed so as to permit the enclosed hand to freely receive and hold a rattle and the like.

7. An anti-thumb-sucking device for infants comprising a cuff of semi-rigid material of a size to enclose a baby's hand and extend outwardly beyond the same, said cuff provided with means at one end of the cuff for securing around the wrist, the outer end of the cuff being open and unobstructed so as to permit the enclosed hand to freely receive and hold a rattle and the like.

8. An anti-thumb-sucking device for infants comprising a cuff of transparent semi-rigid sheet material adapted to fit over the hand of an infant in generally encircling relation thereto and formed to terminate in opposite inner and outer open ends at points adjacent the wrist and outer ends of the fingers respectively, the outer open end being of a diameter at least that of the greatest thickness of the enclosed hand to enable the hand within the cuff to freely receive a rattle or the like, a flexible band secured to the cuff adjacent the inner end thereof arranged and adapted to closely fit around the wrist of the infant for securing the cuff in place over the hand.

9. An anti-thumb-sucking device for infants comprising a cuff of semi-rigid sheet material adapted to loosely fit over the hand of the infant in a generally encircling relation thereto, said cuff being of a size to terminate in opposite outer and inner end edges at points adjacent the wrist and outer ends of the fingers respectively of the infant thereby leaving the outer end of the cuff adjacent the ends of the fingers open to enable the enclosed hand to freely receive a rattle or the like and flexible wrist engaging means on the cuff formed with ventilating openings, said means being arranged and adapted to connect between the wrist of the infant and the cuff, for securing the cuff in position on the enclosed hand while permitting substantially free movement of the hand within the cuff.

10. Means for securement to the wrist of an infant to prevent thumb-sucking while permitting free movement of the fingers therewithin and permitting the grasping of objects by said fingers when the objects are of such size as can be inserted within said means, comprising a cuff having a circumference at one end corresponding to the circumference of an infant's wrist, means secured on said one end for securing the said end to an infant's wrist, the circumference of the other end of said cuff being sufficient to permit the hand to grasp objects therewithin, but of a circumference such that the infant cannot touch the ends of its fingers with its lips, the cuff being open ended at said second end and of a length to extend over the finger tips when extended and when said one end is secured to the wrist.

11. An anti-finger-sucking device for infants comprising a cuff of transparent semi-rigid material of a size to enclose a baby's hand and to extend outwardly beyond the same, said cuff provided with means at one end thereof for securing around the wrist, the outer end of the cuff being open and unobstructed so as to permit the enclosed hand to freely receive and hold a rattle and the like, the said outer end edges being provided with a protective edging.

12. An anti-finger-sucking device for infants comprising a cuff of transparent semi-rigid material of a size to enclose a baby's hand and to extend outwardly beyond the same, said cuff being provided with means at one end thereof for securing around the wrist, the outer end of the cuff being open and unobstructed so as to permit the enclosed hand to freely receive and hold a rattle or the like, portions of the material of said cuff along one side thereof being held in overlapping relation, means for holding said portions in overlapping relation and means secured to the exposed edges of said material at the outer end of the cuff to prevent scratching or cutting by such edges.

13. An anti-thumb sucking device of the character described comprising an open-ended generally tubular member of sheet material adapted to substantially enclose the hand of a baby with one end terminating at the wrist and the opposite end terminating outwardly of the ends of the fingers of the hand, flexible means at the end of said member adjacent the wrist for securing said end to the wrist, and the edge of the member at the opposite end provided with a protective beading forming a rounded edge arranged and adapted to insure against injury from contact with an exposed, relatively sharp edge at said opposite end.

14. An anti-thumb-sucking device of the character described comprising an open-ended, elongated tubular member of sheet material having overlapped margins along one side and an edging of relatively soft material secured to and covering the edges of the member at one end and covering the free edge of the overlying margin along said side, said device being of a diameter to loosely surround the hand of a baby with said one end terminating outwardly of the ends of the fingers and the opposite end terminating at the wrist, means at said opposite end arranged and adapted to removably secure said end to the wrist.

BERNIECE MOLLER.